(12) United States Patent
Geafer et al.

(10) Patent No.: US 11,644,660 B2
(45) Date of Patent: May 9, 2023

(54) COOLING DEVICE FOR AN ENDOSCOPE OR AN EXOSCOPE

(71) Applicant: KARL STORZ SE & Co. KG, Tuttlingen (DE)

(72) Inventors: Lawrence Geafer, Tuttlingen (DE); Andreas Heni, Tuttlingen (DE); Markus Kupferschmid, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 334 days.

(21) Appl. No.: 17/080,074

(22) Filed: Oct. 26, 2020

(65) Prior Publication Data

US 2021/0132361 A1 May 6, 2021

(30) Foreign Application Priority Data

Nov. 5, 2019 (DE) ...................... 10 2019 129 815.6

(51) Int. Cl.
  *G02B 23/24* (2006.01)
  *A61B 1/12* (2006.01)
  *H05K 7/20* (2006.01)

(52) U.S. Cl.
  CPC ............ *G02B 23/2476* (2013.01); *A61B 1/12* (2013.01); *H05K 7/20336* (2013.01); *H05K 7/20454* (2013.01)

(58) Field of Classification Search
  None
  See application file for complete search history.

(56) References Cited

U.S. PATENT DOCUMENTS

| 2009/0315986 A1* | 12/2009 | Ohara ...................... A61B 1/05 348/E7.085 |
| 2011/0237886 A1 | 9/2011 | Yamamoto et al. |

(Continued)

FOREIGN PATENT DOCUMENTS

| CN | 103476319 A | 12/2013 |
| CN | 104010557 A | 8/2014 |

(Continued)

OTHER PUBLICATIONS

German Search Report for German Application No. 10 2019 129 815.6, dated Jun. 5, 2020.

(Continued)

*Primary Examiner* — Heather R Jones
(74) *Attorney, Agent, or Firm* — Jason H. Vick; Sheridan Ross, PC

(57) ABSTRACT

A cooling device is provided having a heat source arranged on a support element, the support element arranged on a rigid heat barrier element and the heat barrier element arranged on a housing such that the support element, the heat barrier element and the housing form a mechanically rigid unit, the heat barrier element having a low heat conductivity, wherein a heat conducting element, arranged between the housing and the support element, bears against a first surface of the support element with a second surface and faces a fourth surface of the housing with a third surface, wherein the heat conducting element has a high heat conductivity, the second surface is at an angle to the third surface, and the heat conducting element is formed separately from the support element and the housing.

20 Claims, 7 Drawing Sheets

(56) References Cited

U.S. PATENT DOCUMENTS

| | | |
|---|---|---|
| 2013/0137925 A1 | 5/2013 | Ushijima et al. |
| 2014/0206939 A1 | 7/2014 | Eisele et al. |
| 2014/0303439 A1 | 10/2014 | Scherr et al. |
| 2016/0278620 A1* | 9/2016 | Kawayoke ........... H04N 5/2253 |
| 2017/0071462 A1 | 3/2017 | Wieters et al. |

FOREIGN PATENT DOCUMENTS

| | | |
|---|---|---|
| CN | 106233183 A | 12/2016 |
| CN | 109124548 A | 1/2019 |
| DE | 102016014247 A1 | 5/2018 |
| JP | 2012-050704 A | 3/2012 |

OTHER PUBLICATIONS

European Search Report for corresponding European Application No. 20191125.2, dated Jan. 22, 2021.
First Office Action (Including Translation) for corresponding Chinese Patent Application No. 202011184538.4, dated Jun. 15, 2022.
Notification of Grant of Rights for Invention Patent (Including Translation) for corresponding Chinese Patent Application No. 202011184538.4, dated Jan. 11, 2023.

* cited by examiner

COOLING DEVICE FOR AN ENDOSCOPE OR AN EXOSCOPE

CROSS-REFERENCE TO RELATED APPLICATION

This application claims priority from German patent application 10 2019 129 815.6, filed on Nov. 5, 2019. The entire contents of this priority application are incorporated herein by reference.

BACKGROUND

The present disclosure relates to a cooling device for an endoscope or an exoscope and a system with a cooling device.

Scopes, such as endoscopes and/or exoscopes, passively dissipate the heat generated by light loss and electrical losses via their respective surfaces. This passive dissipation causes these instruments to heat up as a whole. Corresponding design efforts to dissipate the heat have focused on ensuring that the surface temperatures reached during operation are below the maximum temperatures defined in the DIN EN 60601-1 standard.

US 2016/0278620 A1, according to its abstract, discloses an image pickup apparatus that includes an image pickup device on which a light receiving section is formed, a heat transfer member made of a material having heat, or thermal, conductivity equal to or higher than 15 W/(m·K), the heat transfer member including a wiring board, a joining section joined to the image pickup device, a bending section extended from the joining section, and a fixed section extended from the bending section, and a housing made of metal, an inner surface of which is in contact with a part of the fixed section of the heat transfer member housed on an inside.

DE 10 2016 014 247 A1, according to its abstract, discloses a video endoscope comprising at least one internal heat source, with a latent heat storage for receiving at least part of the heat generated by the at least one internal heat source via a heat transport path formed between the at least one internal heat source and the latent heat storage, wherein a thermal resistance element is arranged in the heat transport path to increase a thermal resistance. Thereby it can be achieved in particular that the videoendoscope can be operated over a longer period of time without a surface of a housing of the videoendoscope exceeding a predetermined maximum temperature.

BRIEF SUMMARY

It is one object to provide an improved cooling device for a scope, such as an endoscope or an exoscope, which provides sufficient cooling with a low constructional effort.

According to one aspect, there is provided a cooling device for a scope (e.g., an endoscope or an exoscope, etc.), the cooling device comprising a heat source (e.g., at least one image sensor, etc.) arranged on a support element, the support element being arranged on a rigid heat barrier element and the heat barrier element being arranged on a housing in such a way that the support element, the heat barrier element and the housing form a mechanically rigid unit, the heat barrier element having a low heat, or thermal, conductivity, wherein further disposed between the housing and the support element is a heat conductive member, a first surface of the support element having a second surface, a third surface of the heat conductive member facing a fourth surface of the housing, wherein the heat conductive member has a high heat, or thermal, conductivity, the second surface is at an angle to the third surface, and the heat conductive member is formed separately from the support element and the housing.

The inventors recognized that compliance with the DIN EN 60601-1 standard is of course an important aspect, but that the heating of the electrical components, especially the image sensors, is a limiting factor in image quality. This depends on the operating temperature, because the warmer the electrical components become, the more dark current noise is generated. The data sheets for the electrical components, such as the image sensors, specify maximum temperatures at which "good" image quality is still guaranteed.

Especially for exoscopes, in particular those that are not held in the hand, the temperatures allowed for sufficient cooling of the entire system are usually higher than the surface temperatures allowed for instruments according to the standard DIN EN 60601-1, which surprisingly allows passive heat dissipation (by heat conducting and free convection) of the image sensors. Exoscopes are usually also more powerful, i.e. they produce more power dissipation than endoscopes, which means that the higher surface temperatures are indeed reached. However, in the state of the art this has prevented passive cooling of the installed image sensors, as these, as a heat source, must always be warmer than the surrounding components in order to be able to transfer the heat loss to them.

One of the special features of the proposed cooling device is that the mechanical coupling of the heat source (e.g., image sensors, etc.) relative to the housing is separated from the thermal coupling of the heat source to the housing. This is achieved on the one hand by the fact that the support element, the heat barrier element and the housing form a mechanically rigid unit, wherein the heat barrier element has a low heat conductivity. On the other hand this is achieved by the fact that the heat conducting element, which is placed between the housing and the support element, has a high heat, or thermal, conductivity.

The term "rigid" should be understood to mean that the arrangement of the support element, heat barrier element and housing remains at least essentially unchanged if the heat conducting element is placed between the support element and the housing during manufacture. The aim of this rigidness is that both the second surface of the heat conducting element is pressed against the first surface of the support element and the third surface of the heat conducting element is pressed towards or against the fourth surface of the housing. In this way, the respective surfaces lie firmly against each other and allow a good heat flow from the heat source via the heat conducting element to the housing.

The terms "low heat conductivity" and "high heat conductivity" are to be understood as meaning that by means of the low heat conductivity a heat flow via the heat barrier element to the housing is at least essentially kept low or prevented and that by means of the high heat conductivity a heat flow via the heat conducting element to the housing is to be promoted. The terms "heat conductivity" and "thermal conductivity" may be used interchangeably herein and may refer to an ability of a material to conduct heat. As can be appreciated, a component having a low heat conductivity transfers heat at a lower rate (e.g., W/(m·K), etc.) than a component having a high heat conductivity, and vice versa. In some embodiments, a component having a low heat conductivity may correspond to a temperature, or heat, insulator, while a component having a high heat conductivity may correspond to a temperature, or heat, conductor. A goal is it in particular that the entire heat flow from the heat source to the housing takes place to at least 80%, or at least 85%, or at least 90% or at least 95% over the heat conducting element. For some embodiments this value is at least 97%, or at least 99%, or at least 99.5% or at least 99.9%.

When choosing the materials for the heat conducting element and the heat barrier element, the skilled person is guided by the desired rigidness and the minimum proportion of the heat flow to be conducted through the heat conducting element. In principle, a large number of material combinations can be considered, provided that the aspect of separation between mechanical coupling and thermal coupling can be realized.

The feature that the heat conducting element is configured separately from the support element and the housing, and that the second surface is at an angle to the third surface, makes it possible to achieve a simple constructional design, which at the same time allows good heat transfer from the heat source to the housing as a heat sink.

In some exemplary embodiments, the heat conducting element is inserted between the support element and the housing when the cooling device is assembled. Due to the angle between the second and third surfaces, similar to an inclined plane, the heat conducting element first comes into physical contact and then, as it is pushed further in, begins to exert a force on the housing and the support element. However, since these elements are rigid and their position relative to each other does not, at least in essentially change, these elements now exert a counterforce on the heat conducting element. As a result, the first surface is pressed against the second surface and the third surface is pressed towards or against the fourth surface. This results in a particularly good heat flow. Due to the angle, tolerances within the structure can be compensated.

In some exemplary embodiments, the second surface and/or third surface is also at an angle to the fourth surface. In this way, the cooling device can easily be configured to the respective application situation. In other preferred embodiments, the first surface is parallel to the second surface, and/or the third surface is parallel to the fourth surface. This enables a particularly good contact between these two pairs of surfaces.

Some exemplary embodiments use a thermoelectric cooling module that directly cools the heat source, especially image sensors. The thermoelectric cooling module may correspond to a type of heat pump that extracts heat from one location and transports it to another location. For this purpose, power must be provided, which must be dissipated in the form of additional heat. In this case the additional heat is passively transferred to the housing, which then continues to heat up and to give off more heat.

In principle, an external, active cooling system (e.g., a heat exchanger, a heat pump, a fluid pump, etc.) can also be used. A cooling medium such as water or air is pumped through tubes into the endoscope or exoscope by an external pump to cool the image sensors. This requires an additional, external device. However, the proposed solution can do without this additional external device. There is also no need to lay any other cables besides the power and data cables and the fiber optic cable, which are perceived as disturbing. In addition, no noise is generated by fluid flows.

In principle, an additional internal, active cooling system can also be used. A fan built into the exoscope provides cooling for the image sensors. In one embodiment, the fan may allow cool air, or other gas, to pass over a portion of the image sensors, support elements, holders, or mounts, or some other physical member that is in contact with a portion of the image sensors. As the air, or gas, passes over these physical elements, the heat generated by the image sensors may be directed away from the image sensors. In some embodiments, the air may be drawn by the fan (e.g., from one environment external to the internal space of the exoscope, etc.) through a filter (e.g., a high-efficiency particulate air filter, etc.) ensuring the air drawn by the fan is clean (e.g., substantially, if not totally, free of dust or other particulate). In this embodiment, external tubes may not be required. However, the proposed solution also offers advantages here, as no noise is generated by the cooling. Furthermore, no particles, especially dust, can enter the endoscope or exoscope and therefore cannot settle on optical components.

In an exemplary embodiment, image sensors are located as a heat source, usually on a circuit board, on an image sensor holder as a support element, via which the alignment and position of the image sensors are adjusted. This support element may be made of aluminum and may effectively conduct the heat from the image sensors to a cooling element. The cooling element is positioned between the image sensor holder and a heat sink, which distributes the heat loss as widely as possible. The image sensor holder touches neither the surrounding parts nor the heat sink, so that the cooling module dissipates only the dissipated heat of the image sensors. Also, any heat backflow from the heat sink to the image sensor holder via the screws is prevented by washers made of material with poor heat conductivity (e.g., washers made from a thermally insulative, nonconductive material, etc.). This is due to the effectiveness of the sensor cooling. The less thermal power the cooling module has to transport, the lower the temperatures on the cold side may become.

In an exemplary embodiment, the heat conducting element is configured to be inserted between the support element and the housing for its positioning, with its second surface sliding onto the first surface of the support element. For instance, the heat conducting element may be inserted into a gap that separates the support element from the housing. When inserted into the gap, a thermal conductivity path may be formed running from the support element through the heat conducting element. In some embodiments, the thermal conductivity path may run from the support element through the heat conducting element to the housing.

This design may be easy (e.g., economical, low-cost, etc.) to implement, or manufacture, in terms of production technology and may ensure good surface contact between the first or second surface.

In an exemplary embodiment, the heat conducting element is wedge-shaped. For example, the heat conducting element may comprise a tapered wedge-shaped section. Among other things, this tapered wedge-shaped section may allow for quick assembly providing a lead-in angle for the heat conducting element as it is inserted into the gap between the support element (e.g., support bracket, etc.) and an inside wall of the housing.

This embodiment is easy to realize in terms of production technology and ensures good surface contact between the first or second surface. Providing a wedge-shaped section to the heat conducting element having a first angled surface and a mating angled surface of the support element ensures that as the heat conducting element is inserted into the gap, the heat conducting element will seat against the support element filling the gap. In contrast to a design utilizing parallel nonangled surfaces for the heat conducting element, and which would require exact tolerancing of the width of the heat conducting element to be the same size as the gap, the instant design does not require such tolerancing or dimensioning for the width of the heat conducting element. For example, any width of the gap may be accommodated by inserting the heat conducting element until the angled surfaces (e.g., of the heat conducting element and the support element contact one another and the gap is filled.

In an exemplary embodiment, the thermally conductive element has a fastening element (e.g., a screw, bolt, rivet, clip, tab, etc., and/or some other type of fastener) with which the thermally conductive element can be fastened to the support element.

This embodiment may ensure that the heat conducting element remains permanently in a defined position and does not shift, especially in view of the thermal changes that always occur. The fastening element is, in some exemplary embodiments, a screw that engages in a thread (e.g., a tapped hole, threaded insert, captured nut, etc.) in the support element.

In an exemplary embodiment, the fastener or fastened interface has a flexible element which is located between the heat conducting element and the support element and is configured to distribute and/or reduce pressure between the heat conducting element and the support element.

This embodiment may enable a particularly good fit of the heat conducting element relative to the support element without exerting excessive pressure on the support element.

In an exemplary embodiment, the housing has a housing cover that covers the arrangement of heat source, support element and heat conducting element.

This embodiment may allow access to the inside of the enclosure during the installation of the cooling device and allows the enclosure to be sealed after installation. Depending on the respective installation situation, the housing cover can follow the shape of the arrangement of heat source, support element and heat conducting element at least approximately and is, in particular, arched and/or spherical.

In an exemplary embodiment, a cooling element is arranged between the heat conducting element and the housing.

This embodiment may enable a higher heat flow away from the heat source.

In an exemplary embodiment, the cooling element is configured as a Peltier cooler (e.g., a thermoelectric cooler, etc.). The Peltier cooler may correspond to a thermoelectric cooler that operates by the Peltier effect. In some embodiments, the Peltier cooler may have a "heat-emitting" side and "cooling" side. For example, when electric current flows through the Peltier cooler, heat is transferred from one side to the other side such that the cooling side lowers in temperature and the heat-emitting side increases in temperature.

This embodiment may make it possible to achieve an even higher heat flow away from the heat source. The Peltier cooler faces, with its cooling side, the heat source and, with its heat-emitting side, the housing. The reduced temperature on the side of the heat source increases the heat flow to the Peltier element. The increased temperature on the side of the housing increases the heat flow away from the Peltier element.

In an exemplary embodiment, the second surface has a first surface section and a second surface section that are at an angle to each other.

This embodiment may make it easier to assemble and manufacture.

In an exemplary embodiment, the heat barrier element is made of or comprises one of the materials selected from the group consisting of plastic, stainless steel, and titanium.

These materials have proven to be advantageous for the heat barrier element in practical tests.

In an exemplary embodiment, the thermally conductive element has or is formed from one of the materials selected from the group consisting of aluminum, aluminum alloy, copper, and copper alloy.

These materials have proven to be advantageous for the heat conducting element in practical tests.

According to a second aspect, there is provided a system with a previously described cooling device, wherein a second heat source is arranged inside the housing in addition to the first heat source mentioned above.

In this embodiment, the system has a second heat source, which is the heat loss of an electronic component, for example a Field Programmable Gate Array (FPGA), or light loss. In particular it is assumed that the second heat source has a higher temperature than the first heat source. This means that additional heat is generated inside the package, which could heat the first heat source, for example one or more image sensors. Due to the good heat flow from the first heat source to the housing, additional heating of the first heat source can be reduced or prevented.

In an exemplary embodiment, the second heat source is located directly on the housing.

This arrangement means that a considerable part of the heat energy emitted by the second heat source reaches the housing directly and is dissipated from there, for example via the air.

In an exemplary embodiment, the second heat source is connected to a heat distributor, which is configured to increase a heat flow from the heat source to the housing.

In this way a remaining heat flow from the second heat source to the first heat source may be reduced. Thus an additional warming of the first heat source may be reduced or prevented. In addition the heat distributor may offer the possibility of distributing a developing heat on a larger surface to thus avoid punctually hot sites, also called hot spots, at the surface.

In an exemplary embodiment, the heat distributor has a holder on which a heat pipe is mounted, with the heat pipe running along the housing.

This design may increase the heat flow from the second heat source to the housing. Thus as a result a remaining heat flow from the second heat source to the first heat source may be reduced. An additional warming of the first heat source may be reduced or prevented in such a way.

BRIEF DESCRIPTION OF THE DRAWINGS

It goes without saying that the features mentioned above and the features to be explained below can be used not only in the combination indicated in each case, but also in other combinations or in isolation, without leaving the scope of the present disclosure. The figures show.

BRIEF DESCRIPTION OF EXEMPLARY EMBODIMENTS

Figure 1:
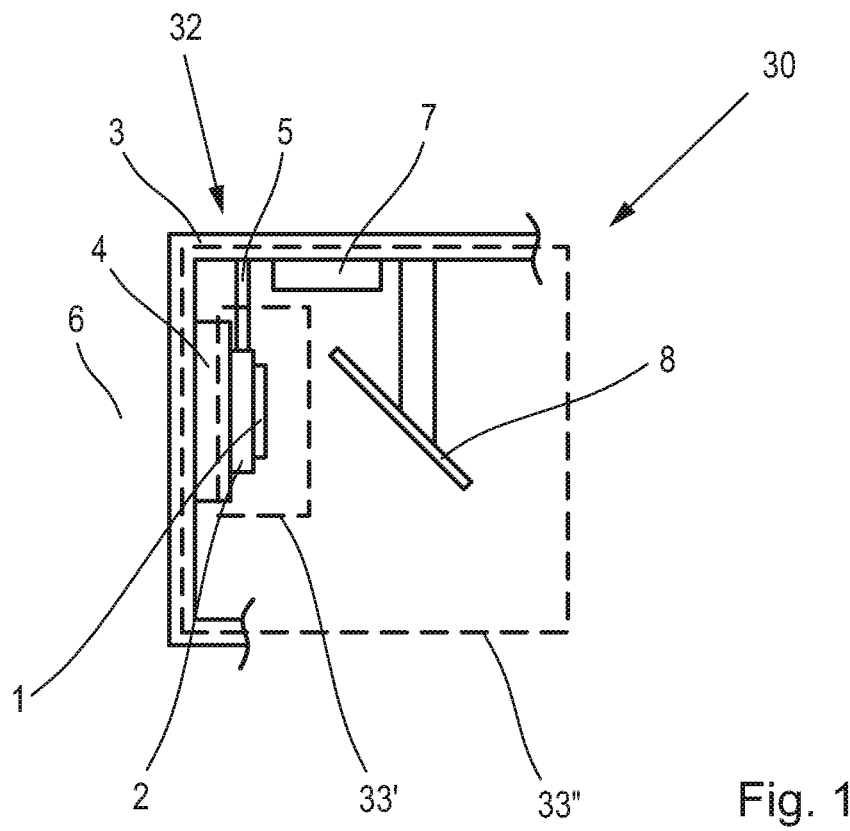
FIG. 1 an embodiment of a system with a cooling device.

FIG. 1 shows a system 30 with a cooling device 32, where a first heat source 1 and a second heat source 7 are arranged inside a housing 3. The housing 3, comprising at least one wall, or side, separates an interior environment from an exterior environment (e.g., the environment of the housing 6). It is desired that a first temperature zone 33' is formed around the first heat source 1, whereas a second temperature zone 33" is formed within the housing 3, whose temperature is or may be higher than that of the first temperature zone 33'. Only as an example, optical components 8 are shown inside the second temperature zone 33", but outside the first temperature zone 33'. In some embodiments, the housing 3 may physically separate, and even isolate, the first temperature zone 33" from the environment of the housing 6 (e.g., the environment surrounding at least a portion of the housing 3, etc.). The system 30 comprises a cooling element 4 that physically contacts the housing 3 and a support element 2 (e.g., a support bracket, etc.) of the first heat source 1. In one embodiment, the support element 2 may be arranged on, or attached to, a heat barrier element 5. The heat barrier element 5 may be rigidly attached to the housing.

In the following, the design of the cooling unit 32 will be described in more detail.

Figure 2:
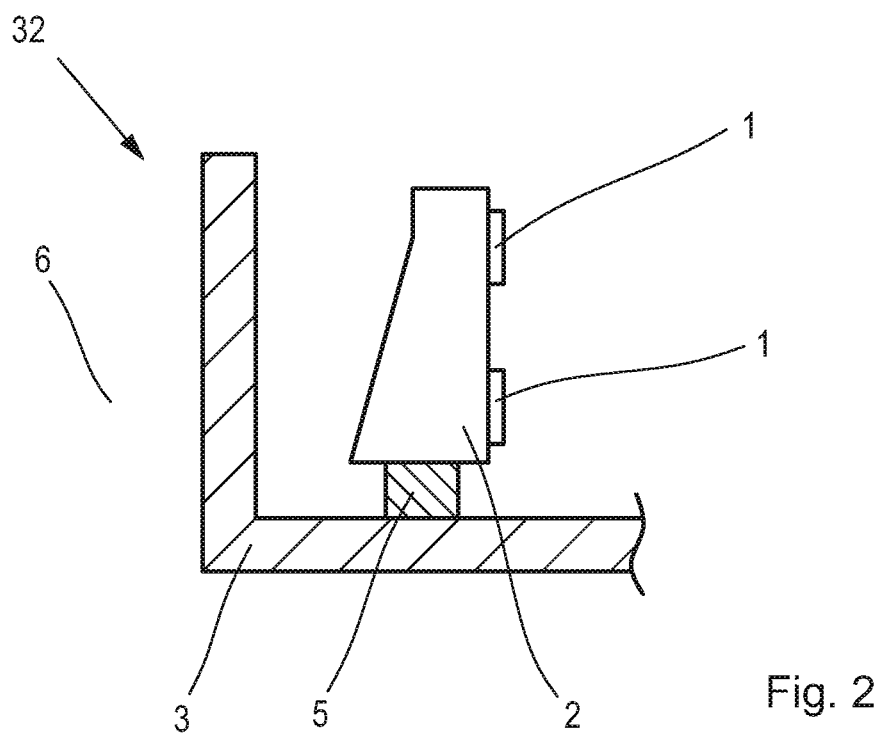
FIG. 2 a first step in assembling a cooling device according to a first embodiment.

FIG. 2 shows the first step in assembling a first embodiment of a cooling device 32. Shown here are two heat sources 1, which are each configured as an image sensor or a light emitting diode (LED). Although shown as an image sensor or an LED in FIG. 2, it should be appreciated, that the heat source 1 may correspond to any electronic device or circuit that generates heat while powered, while being attached to a powered circuit, and/or while being operated. Examples of the heat source 1 as described herein may include, but are in no way limited to, one or more chips, circuit boards, image sensors (e.g., CMOS image sensors, etc.), inductors, integrated circuits, LEDs, processors, relays, resistors, transformers, transistors, etc. The heat sources 1 are arranged on a support element 2 (e.g., on a mount surface), wherein the support element 2 is arranged on a rigid heat barrier element 5. The support element 2 may correspond to a mount plate, block, or bracket (e.g., support bracket) for the heat sources 1. In one embodiment, the support element 2 may be formed from a metal or metal alloy (e.g., by machining, casting, molding, and/or otherwise forming the material through one or more operations, etc.). In one embodiment, the heat sources 1 may be bonded, or adhered, to the support element 2. In some embodiments, the heat sources 1 may be fastened to, or formed on, the support element 2. A thermal interface material may be arranged between a surface of the support element 2 and a surface of the heat sources 1. An environment 6 of the housing 3 is also shown in FIG. 2.

The heat barrier element 5 is arranged on the housing 3 in such a way that the support element 2, the heat barrier element 5 and the housing 3 form a mechanically rigid unit. The heat barrier element 5 has a low heat conductivity. This ensures a stable mechanical arrangement of the heat sources 1 relative to the housing 3. The heat barrier element 5 may correspond to a heat isolation standoff, or other protrusion, that extends from the housing 3 to the support element 2. The heat barrier element 5 may provide a rigid and thermally-insulated mount interface between the housing 3 and the support element 2. Stated another way, the heat barrier element 5 may prevent or inhibit the transfer of heat from the support element 2 to the housing 3. In some embodiments, the heat barrier element 5 may be made from a ceramic, plastic, fiberglass, composite, or other thermally-insulative material. Additionally or alternatively, the heat barrier element 5 may include an athermalized structure that rigidly supports the support element 2 relative to the housing 3. The support element 2 may be attached to the heat isolation standoff (e.g., heat barrier element 5) in the interior environment of the housing 3.

Figure 3:
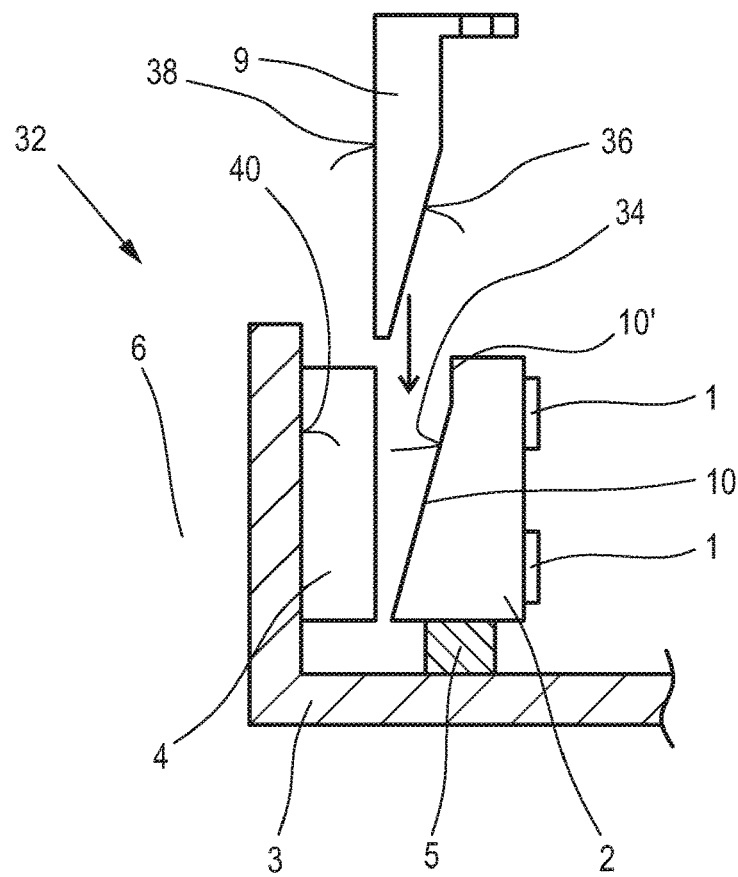
FIG. 3 a second step in the assembling of the first embodiment of cooling device.

FIG. 3 shows a second step in the assembling of the cooling unit 32. The figure shows a first surface 34 of the support element 2, a second surface 36 of the heat conducting element 9, a third surface 38 of the heat conducting element 9 and a fourth surface 40 of the housing 3. The first surface 34 of the support element 2 has a first surface section 10 and a second surface section 10', which are arranged at an angle to each other. The first surface 34 of the support element 2 may be separated a distance from an inside wall (e.g., the fourth surface 40, etc.) of the housing 3 and/or a surface of a cooling element 4, providing a gap between the support element 2 and the inside wall of the housing 3. Opposite the first surface 34 of the support element 2 the heat source 1 may be attached to a mount surface of the support element 2.

It can also be seen that the second surface 36 of the heat conducting element 9 is arranged at an angle to the third surface 38. The heat conducting element 9 is configured separately from the support element 2 and housing 3. The heat conducting element 9 has a high heat conductivity. While the heat barrier element 5 may have a first thermal conductivity (e.g., a low heat conductivity), the heat conducting element 9 may have a second thermal conductivity (e.g., a high heat conductivity) that is higher than the first thermal conductivity. In this manner, the heat barrier element 5 may act as a heat isolation standoff and the heat conducting element 9 may act as a heat conductor, or heat conducting block. In some embodiments, the heat conducting element 9 may correspond to a formed block, bar, or plate of material (e.g., metal, metal alloy, composite, etc.). The arrow indicates that the heat conducting element 9 is inserted between the support element 2 and the housing 3, in this case between the support element 2 and a cooling element 4. For instance, the support element 2 (rigidly attached to the housing 3 via the heat barrier element 5) may be disposed at a distance from the fourth surface 40 of the housing 3 and/or the cooling element 4 such that an open space, or gap, is arranged between the support element 2 and the cooling element 4. The heat conducting element 9 may be inserted into this open space and, when fastened in place, may physically contact at least one surface of the cooling element 4 as well as at least one surface (e.g., first surface section 10, second surface section 10', etc.) of the support element 2. In some embodiments, this physical contact may provide a thermal conduction path running from the support element to the cooling element 4, and/or vice versa. In one embodiment, the heat conducting element 9, when inserted into the gap between the support element 2 and the inside wall of the housing 3, slides along and contacts the first surface 34 of the support element 2 while the third surface 38 faces the inside wall (e.g., the fourth surface 40, etc.) of the housing 3 and a thermal conductivity path is formed (as shown in FIG. 4) running from the support element 2 through the heat conducting element 9 to the housing 3.

As shown in FIG. 3, the heat conducting element 9 may be wedge-shaped including at least one angled, or wedge, portion. The angled, or wedge-shaped, portion may serve as an alignment guide during assembly acting as a tapered lead-in for inserting the heat conducting element 9 into the space between the support element 2 and the cooling element 4. In some cases, the angled portion may provide an increased surface area contact between the heat conducting element 9 and the support element 2 (e.g., when compared to a non-angled interface between the heat conducting element 9 and the support element 2). Furthermore, the heat conducting element 9 is configured to be inserted between the support element 2 and the housing 3 for its positioning and to slide with the second surface 36 along and onto the first surface 34 of the support element 2.

Figure 4:
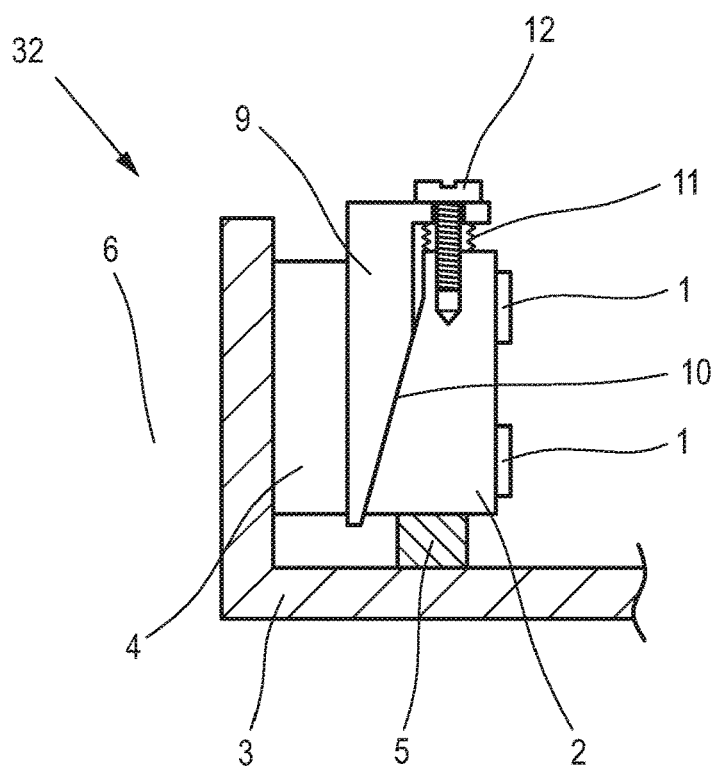
FIG. 4 a third step in the assembling of the first embodiment of the cooling unit.

FIG. 4 shows a third step in the assembling of the cooling device 32, where the heat conducting element 9 is now inserted between the support element 2 and the housing 3, more precisely between the support element 2 and the cooling element 4. In this position, the heat conducting element 9 is in contact with the first surface 34 of the support element 2 with its second surface 36 and is facing the fourth surface 40 of the housing 3 with its third surface 38. In this position, a thermal conductivity path is formed running from the support element 2 through the heat conducting element 9 to the housing 3. In one embodiment, the thermal conductivity path may be formed running from the support element 2 through the heat conducting element 9 and through the cooling element 4 to the housing 3.

For a stable positioning, the heat conducting element 9 has a fastening element 12, here a screw, with which the heat conducting element 9 is fastened to the support element 2. The fastening element 12 has a flexible element 11, which is arranged between the heat conducting element 9 and the support element 2. The flexible element 11 is configured to distribute and/or reduce a pressure between the heat conducting element 9 and the support element 2. Examples of the flexible element 11 may include, but are in no way limited to, one or more compliant washers such as rubber washers, plastic washers, polyurethane washers, etc., disk springs (e.g., Belleville springs, etc.), gaskets, O-rings, spring washers, surgical tubing, and/or some other compressible preload member.

Figure 5:
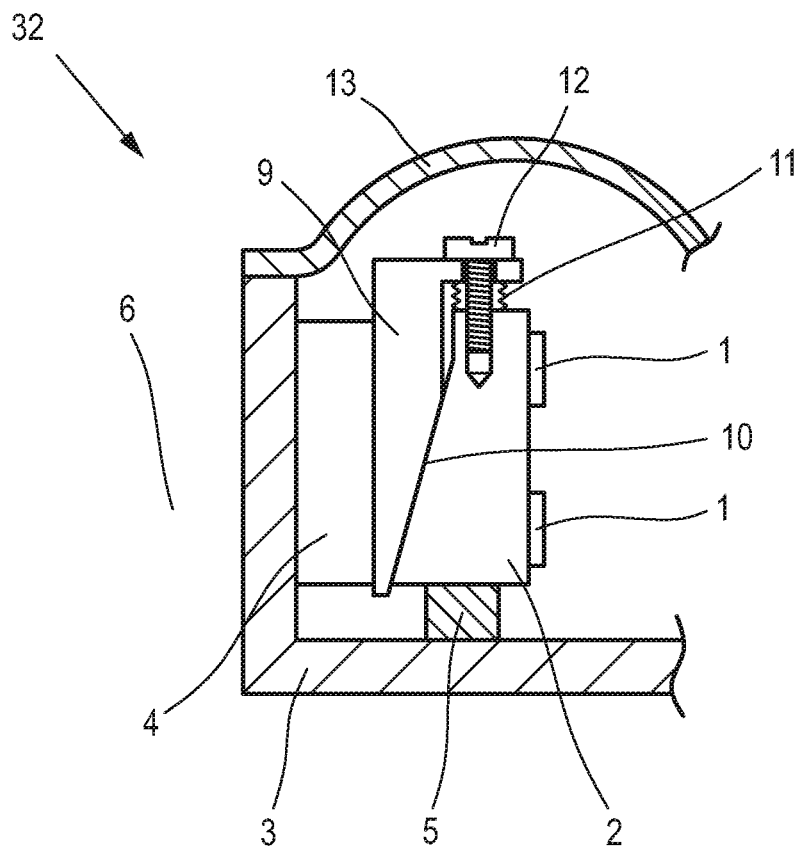
FIG. 5 a fourth step in the assembling of the first embodiment of the cooling unit.

FIG. 5 shows a fourth step in the assembling of the cooling device 32, where a housing cover 13 has now been placed to cover the arrangement of heat sources 1, support element 2 and heat conducting element 9. Furthermore, the housing cover 13 also covers the cooling element 4 in this embodiment. In some embodiments, the housing cover 13 may be fastened, adhered, or otherwise attached to the housing 3.

Figure 6:
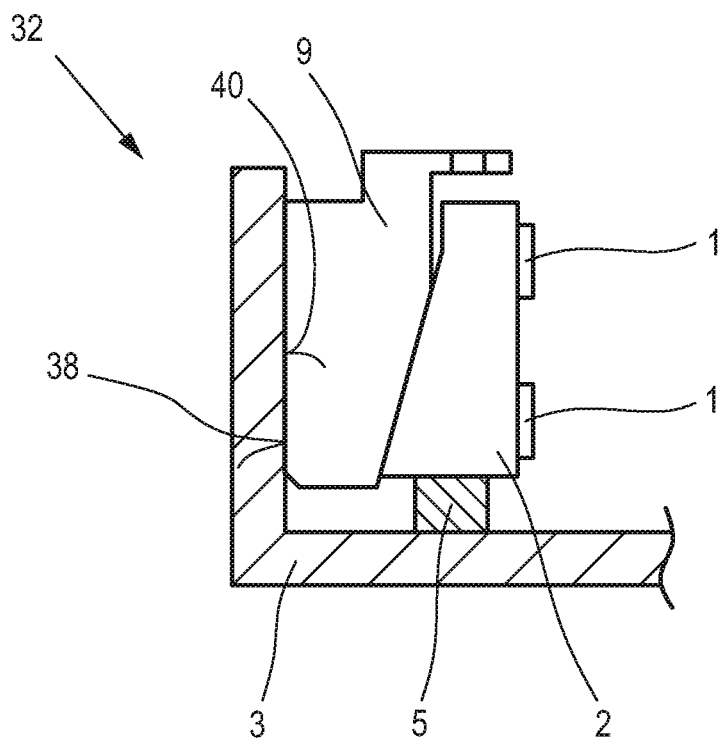
FIG. 6 a second embodiment of a cooling device.

FIG. 6 shows a second embodiment of the cooling device 32, in which the heat conducting element 9 with its third surface 38 is in direct contact with the fourth surface 40 of the housing 3. The heat conducting element 9 shown in FIG. 6 is inserted into the space between the support member 2 and the housing 3 as described above.

Figure 7:
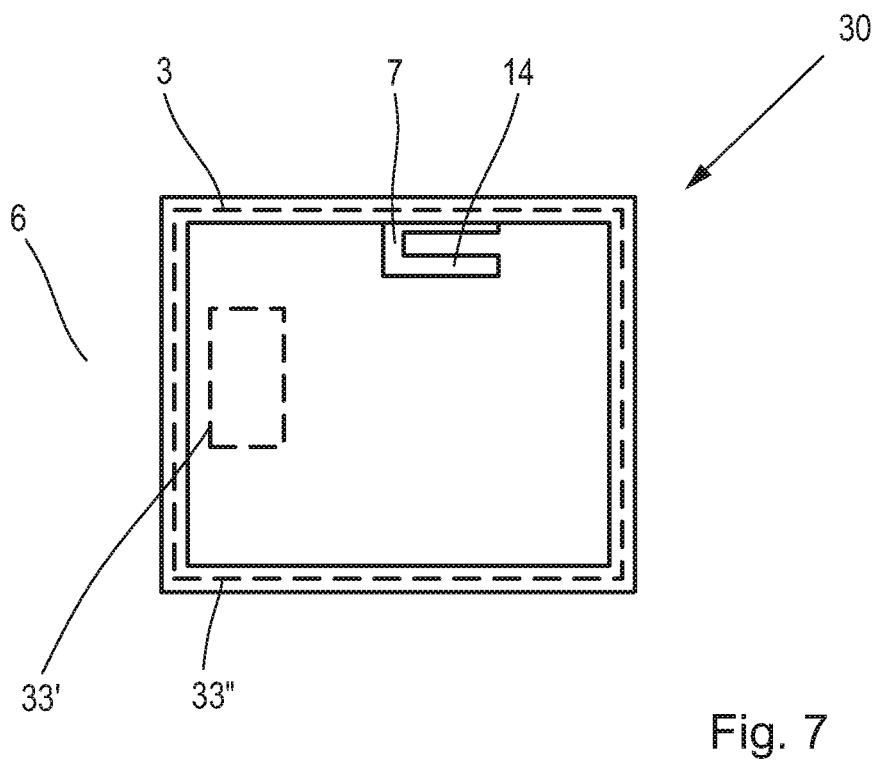
FIG. 7 a second embodiment of a system with a cooling device.

FIG. 7 shows a symbolic, or schematic, representation of housing 3 in an environment 6, where inside the housing 3 the first temperature zone 33' and the second temperature zone 33" are shown. In addition, a second heat source 7 is shown again. Here the second heat source 7 is located directly at the housing 3. Examples of the second heat source 7 may include, but are in no way limited to, one or more chips, circuit boards, image sensors (e.g., CMOS image sensors, etc.), inductors, integrated circuits, LEDs, processors, relays, resistors, transformers, transistors, etc. At the second heat source 7 a holder 14 (e.g., a mount bracket or mount plate) of a heat distributor 42 is arranged, which is shown in the following figure. In some embodiments, the holder 14 may correspond to a clip, comprising at least one recessed area, that receives at least a portion of the heat distributor 42 (e.g., the heat pipe 15, etc.) and maintains the heat distributor 42 close to, or against and in contact with, one or more walls or sides (e.g., surfaces, etc.) of the housing 3.

Figure 8:
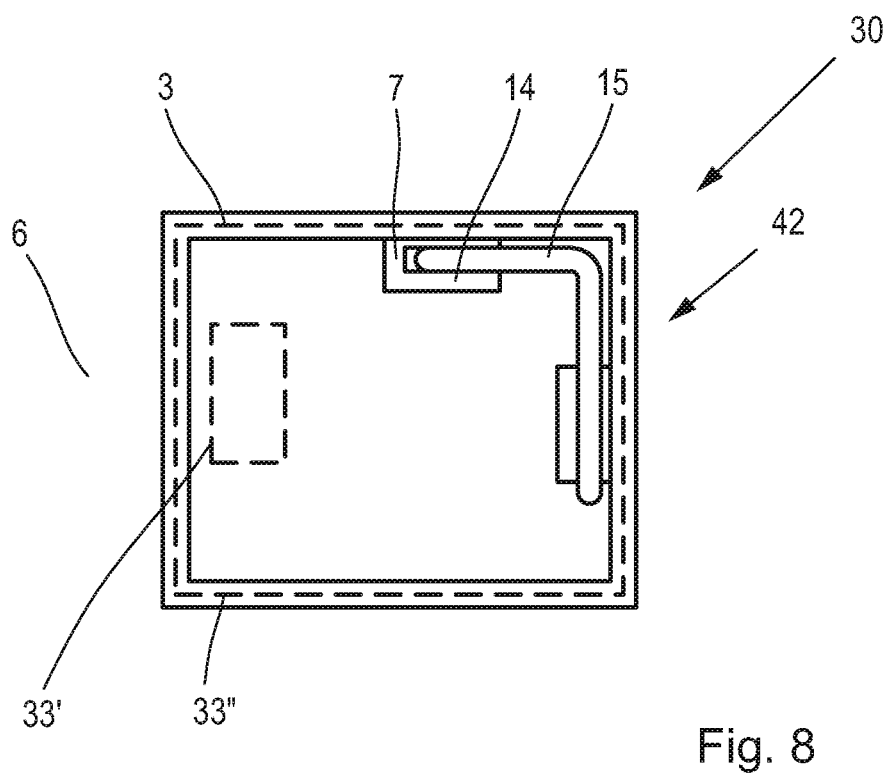
FIG. 8 a third embodiment of a system with a cooling device.

FIG. 8 shows that the second heat source 7 is connected to a heat distributor 42, which is configured to increase a heat flow from the second heat source 7 to housing 3. Here, the heat distributor 42 has a heat pipe 15 which runs along the housing 3. In particular, the heat pipe 15 runs close to at least one wall, or side, of the housing 3 or is arranged on at least one wall, or side, of the housing 3. The improved heat distribution prevents hot spots on the surface. For instance, as heat is generated by the second heat source 7 (e.g., when the second heat source 7 is supplied with some operating voltage, etc.) the heat may be conveyed from the holder 14 along the heat pipe 15 and then the heat may be dissipated, or distributed, along a length of the heat pipe 15. The heat may then transfer from the heat pipe 15 to the housing 3 at one or more areas where the heat pipe 15 is oriented adjacent to, or in contact with, the at least one wall or side of the housing 3. As the heat is distributed over a greater surface area (e.g., via the heat pipe 15, etc.) than the area where the second heat source 7 is disposed in the housing 3, the concentration of heat at this area is prevented and distributed across a greater surface area of the housing 3.

Figure 9:
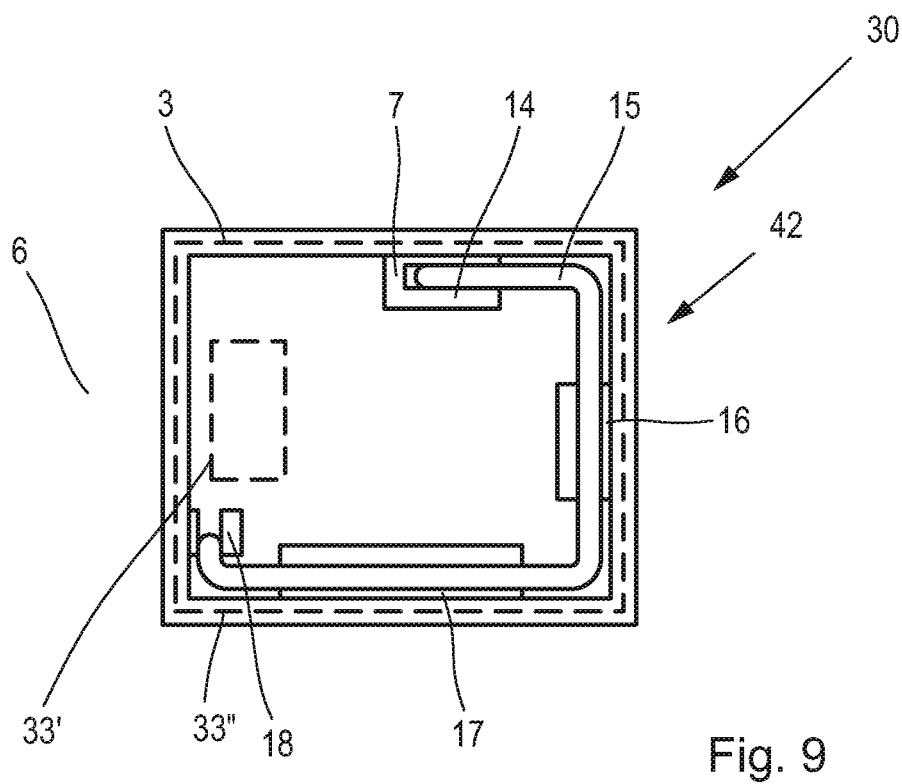
FIG. 9 a fourth embodiment of a system with a cooling device.

FIG. 9 shows a third embodiment of a system 30, wherein the heat pipe 15 is now longer and is guided in further holders 16, 17, 18. Similar to the holder 14, the holders 16, 17, 18 may correspond to one or more clips, brackets, or mount plates that retain a portion of, for example, the heat pipe 15 close to, against, or directly in contact with one or more of the walls or sides the housing 3. The heat generated by the second heat source 7 may be distributed, or spread out, over at least three walls of the housing 3. As shown in FIG. 9, the heat generated by the second heat source 7 can be distributed over a surface area including a portion of each set of opposing walls in the housing 3.

Figure 10:
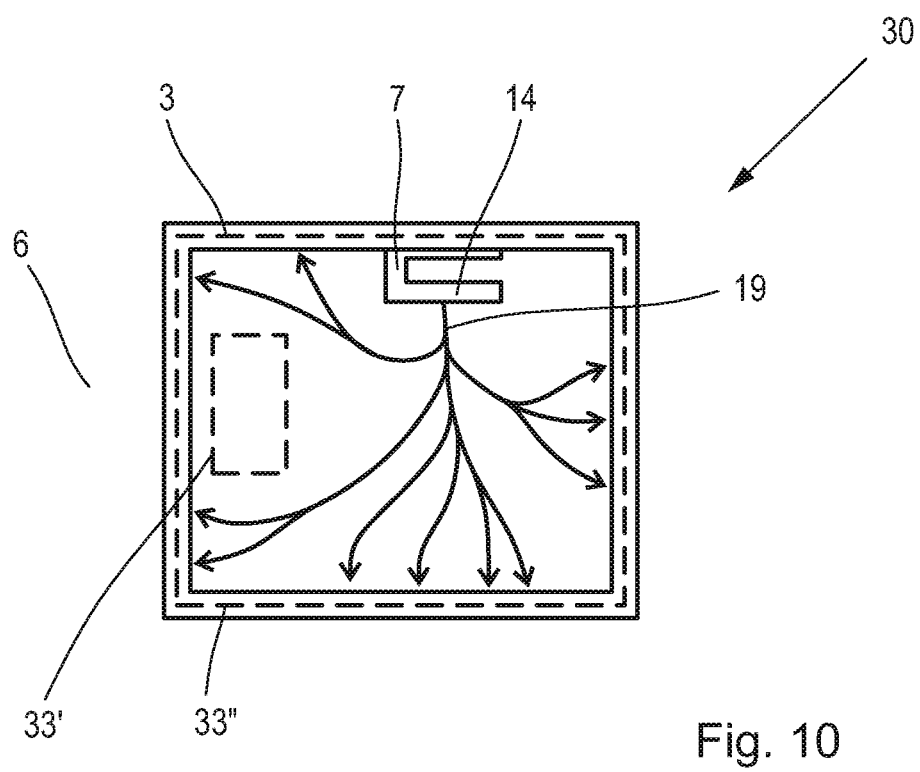
FIG. 10 a simplified representation of the heat flow from the second heat source to the housing in the second embodiment of the system.

FIG. 10 symbolically shows the heat flow from the second heat source 7 to the housing 3. The heat flow is symbolized by arrows 19.

Figure 11:
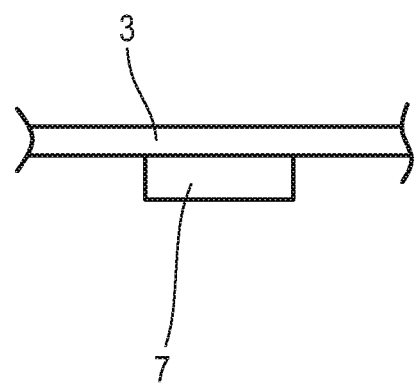
FIG. 11 a first embodiment of an arrangement of a second heat source relative to the housing.

FIG. 11 shows a first embodiment of an arrangement of a second heat source 7 relative to the housing 3. Here the second heat source 7 is arranged directly at the housing 3. For instance, the second heat source 7 may be directly bonded, adhered, or attached to the housing 3 without need of an intermediate mount plate. In some embodiments, a thermal interface, or transfer, material (e.g., tape or paste) may be disposed in between the housing 3 and the second heat source 7.

Figure 12:
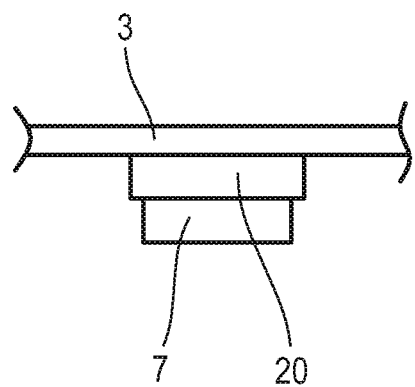
FIG. 12 a second embodiment of an arrangement of a second heat source relative to the housing.

FIG. 12 shows a second embodiment of an arrangement of a second heat source 7 relative to the housing 3. Here the second heat source 7 is attached to the housing 3 by means of a holder 20, wherein the holder 20 is configured for heat transfer. As provided above, the holder 20 may correspond to a plate, clip, or other bracket that interconnects the housing 3 with the second heat source 7.

Figure 13:
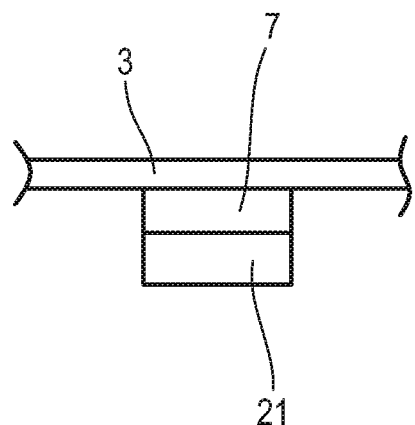
FIG. 13 a third embodiment of an arrangement of a second heat source relative to the housing.

FIG. 13 shows a third embodiment of an arrangement of a second heat source 7 relative to the housing 3. Here, the second heat source 7 is arranged directly on the housing 3. Furthermore, a cooler 21 (e.g., a heat sink, heat dissipation block, etc.) is arranged on the second heat source 7, which is preferably passive.

Figure 14:
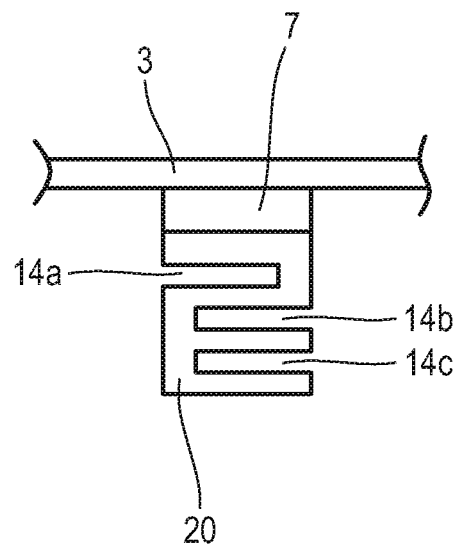
FIG. 14 a fourth embodiment of an arrangement of a second heat source relative to the housing.

FIG. 14 shows a fourth embodiment of an arrangement of a second heat source 7 relative to the housing 3. The holder 20 here is configured in such a way that it has several recesses 14a, 14b, 14c which can be connected with heat pipes. For instance, the several recesses 14a, 14b, 14c may provide respective spaces to receive heat pipes 15. In this embodiment, any heat generated by the second heat source 7 may be dissipated by the housing 3 and dissipated by the heat pipes 15 inserted into the several recesses 14a, 14b, 14c of the holder 20, as described herein.

Figure 15:
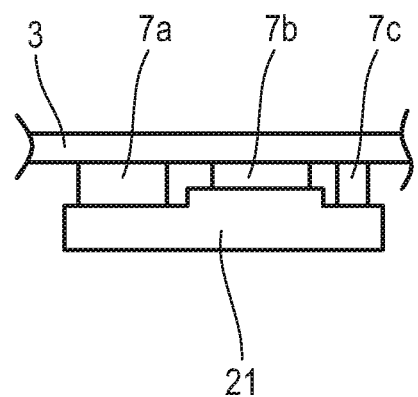
FIG. 15 a fifth embodiment of an arrangement of a second heat source relative to the housing.

FIG. 15 shows a fifth embodiment of an arrangement of a second heat source 7a, 7b, 7c relative to the housing 3. In this configuration, several second heat sources 7a, 7b, 7c dissipate part of their heat to a common cooler 21 (e.g., a heat sink, heat dissipation block, etc.). The common cooler 21 may be in thermal contact with each of the several second heat sources 7a, 7b, 7c. In some embodiments, the common cooler 21 may include a number of machined or formed surfaces that contact the several second heat sources 7a, 7b, 7c arranged at various heights from the housing 3.

It should be noted that the heat source 1, 7 is or has an electrical or electronic component which is supplied with an operating voltage. In some embodiments, the heat source 1, 7 is for example an image sensor, especially a CMOS image sensor.

What is claimed is:

1. A cooling device configured for a scope, wherein the cooling device comprises:
   a heat source arranged on a support element, wherein the support element is arranged on a rigid heat barrier element and the heat barrier element is arranged on a housing wherein the support element, the heat barrier element and the housing form a mechanically rigid unit, and the heat barrier element has a low heat conductivity,
   a heat conducting element arranged between the housing and the support element when assembled, and the heat conducting element abuts a first surface of the support element with a second surface and faces a fourth surface of the housing with a third surface, wherein the heat conducting element has a high heat conductivity, the second surface is at an angle to the third surface, and the heat conducting element is formed separately from the support element and the housing,
   wherein a gap separates the support element from the housing in an unassembled slate, and wherein the heat conducting element, when inserted into the gap between the support element and the housing slides with its second surface onto the first surface of the support element and forms a thermal conductivity path running from the support element through the heat conducting element to the housing.

2. The cooling device according to claim 1, wherein the heat conducting element is wedge-shaped.

3. The cooling device according to claim 1, wherein the heat conducting element has a fastening element that fastens the heat conducting element to the support element.

4. The cooling device according to claim 3, wherein the fastening element comprises a flexible member arranged between the heat conducting element and the support element and distributes a pressure applied by the fastening element fastening the heat conducting element to the support element.

5. The cooling device according to claim 1, wherein the housing has a housing cover that covers the arrangement of the heat source, the support element and the heat conducting element.

6. The cooling device according to claim 1, wherein a cooling element is arranged between the heat conducting element and the housing.

7. The cooling device according to claim 6, wherein the cooling element is configured as a Peltier cooler.

8. The cooling device according to claim 1, wherein the first surface has a first surface section and a second surface section, and wherein the first surface section is angled relative to the second surface section.

9. The cooling device according to claim 1, wherein the heat barrier element comprises one of the materials selected from the group consisting of plastic, stainless steel, and titanium.

10. The cooling device according to claim 1, wherein the heat conducting element comprises one of the materials selected from the group consisting of aluminum, aluminum alloy, copper, and copper alloy.

11. The cooling device according to claim 1, further comprising a second heat source arranged within the housing in addition to the first heat source.

12. The cooling device according to claim 11, wherein the second heat source is arranged directly on the housing.

13. The cooling device according to claim 11, wherein the second heat source is connected to a heat distributor and provides a heat transfer path running from the second heat source to a first location inside the housing that is outside of a heat transfer path running from the second heat source to a second location inside the housing where the second heat source is connected to the housing.

14. The cooling device according to claim 13, wherein the heat distributor comprises a holder on which a heat pipe is arranged, and wherein the heat pipe extends along a length of at least one side of the housing.

15. A cooling device configured for a scope, comprising:
   a housing separating an interior environment from an exterior environment;
   a heat isolation standoff attached to the housing and extending into the interior environment of the housing, the heat isolation standoff having a first thermal conductivity;
   a support bracket attached to the heat isolation standoff in the interior environment of the housing, the support bracket comprising a first surface that is separated a distance from an inside wall of the housing providing a gap between the support bracket and the inside wall of the housing, the support bracket comprising a mount surface that attaches to a heat source of the scope; and
   a heat conducting block having a second thermal conductivity greater than the first thermal conductivity and comprising a first side and a second side, the heat conducting block comprising a second surface disposed on the first side and a third surface disposed on the second side, wherein the heat conducting block, when inserted into the gap between the support bracket and the inside wall of the housing, slides along and contacts the first surface of the support bracket while the third surface faces the inside wall of the housing and forms a thermal conductivity path running from the support bracket through the heat conducting block to the housing.

16. The cooling device according to claim 15, wherein the heat conducting block comprises a tapered wedge-shaped portion disposed between the first and second sides.

17. The cooling device according to claim 15, wherein the heat conducting block inserted into the gap is fastened to the support bracket via a screw fastener, and wherein a compliant washer is disposed between the heat conducting block and the support bracket that distributes a fastening force of the screw fastener across a surface area of at least one of the heat conducting block and the support bracket.

18. A scope cooling system, comprising:
- a housing separating an interior environment from an exterior environment;
- a heat isolation standoff attached to the housing and extending into the interior environment of the housing, the heat isolation standoff having a first thermal conductivity;
- a support bracket attached to the heat isolation standoff in the interior environment of the housing, the support bracket comprising a first surface that is separated a distance from an inside wall of the housing providing a gap between the support bracket and the inside wall of the housing;
- a heat source attached to a mount surface of the support bracket, wherein the heat source, when supplied with an operating voltage, generates an amount of heat; and
- a heat conducting block having a second thermal conductivity greater than the first thermal conductivity and comprising a first side and a second side, the heat conducting block comprising a second surface disposed on the first side and a third surface disposed on the second side, wherein the heat conducting block, when inserted into the gap between the support bracket and the inside wall of the housing, slides along and contacts the first surface of the support bracket while the third surface faces the inside wall of the housing and forms a thermal conductivity path running from the support bracket through the heat conducting block.

19. The scope system according to claim 18, further comprising:
- a second heat source disposed in the interior environment of the housing, wherein the second heat source, when supplied with a second operating voltage, generates a second amount of heat.

20. The scope system according to claim 19, further comprising:
- a mount bracket attached to the housing in the interior environment at a first location, wherein the mount bracket comprises a recessed area and a mount surface, wherein the second heat source is attached to the mount surface of the mount bracket; and
- a heat pipe disposed at least partially within the recessed area of the mount bracket, the heat pipe extending along a length of at least one wall of the housing at a second location apart from the first location in the interior environment, and wherein the second amount of heat generated by the second heat source is distributed to the housing at the first location via the mount bracket and the second location via the heat pipe.

* * * * *